(12) United States Patent
Rowland et al.

(10) Patent No.: US 10,557,949 B2
(45) Date of Patent: Feb. 11, 2020

(54) ACCELERATING FISSILE MATERIAL DETECTION WITH A NEUTRON SOURCE

(71) Applicant: Lawrence Livermore National Security, LLC, Livermore, CA (US)

(72) Inventors: Mark S Rowland, Livermore, CA (US); Neal J Snyderman, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 67 days.

(21) Appl. No.: 15/865,062

(22) Filed: Jan. 8, 2018

(65) Prior Publication Data

US 2018/0188394 A1   Jul. 5, 2018

Related U.S. Application Data

(60) Division of application No. 14/213,502, filed on Mar. 14, 2014, now Pat. No. 9,880,300, which is a continuation-in-part of application No. 12/712,040, filed on Feb. 24, 2010, now Pat. No. 8,891,720, which is a continuation-in-part of application No. 11/233,228, filed on Sep. 21, 2005, now Pat. No. 8,155,258.

(60) Provisional application No. 60/612,968, filed on Sep. 24, 2004.

(51) Int. Cl.
*G01T 3/00* (2006.01)
*G01N 23/00* (2006.01)

(52) U.S. Cl.
CPC ............. *G01T 3/00* (2013.01); *G01N 23/005* (2013.01)

(58) Field of Classification Search
CPC .. G01T 3/00; G01T 3/006; G01T 3/06; G01N 23/005; G01V 5/0091
USPC ................................ 376/159, 170, 180, 254
See application file for complete search history.

(56) References Cited

U.S. PATENT DOCUMENTS

2007/0069146 A1*   3/2007   Neal .......................... G01T 3/06
250/390.11

OTHER PUBLICATIONS

Mihalczo, "Physical description of nuclear materials identification system (NMIS) signatures", Nuclear Instruments and Methods in Physics Research A 450, No. 2-3 (2000): 531-555. (Year: 2000).*

(Continued)

*Primary Examiner* — Jack W Keith
*Assistant Examiner* — Daniel Wasil
(74) *Attorney, Agent, or Firm* — Staniford Tomita

(57) ABSTRACT

A system discriminating fissile material from nonfissile material wherein a digital data acquisition unit collects data at high rate, and processes large volumes of data directly to count neutrons from the unknown source and detect excess grouped neutrons to identify fission. The system includes a Poisson neutron generator for in-beam interrogation of a possible fissile neutron source and inducing neutron emission therefrom, and a DC power supply that exhibits electrical ripple of less than one part per million. A neutron count histogram and Poisson count distribution are overlaid to provide a visual indication of the difference in correlation of natural and induced emitted neutrons from the radiation source to characterize the neutron source as fissile material or non-fissile material.

11 Claims, 9 Drawing Sheets

(56) References Cited

OTHER PUBLICATIONS

Kouzes, "Cosmic-ray-induced ship-effect neutron measurements and implications for cargo scanning at borders", Nuclear Instruments and Methods in Physics Research A 587, No. 1 (2008): 89-100. (Year: 2008).*

* cited by examiner

| Multiplicity | 0 | 1 | 2 | 3 |
|---|---|---|---|---|
| Actual Background | 7209176 | 8463 | 43 | 1 |
| Expected Background | 7209166 | 8481 | 34 | 0 |
| Poisson Distribution | 7209136 | 8541 | 5 | 0 |

ACCELERATING FISSILE MATERIAL DETECTION WITH A NEUTRON SOURCE

CROSS-REFERENCE TO RELATED APPLICATIONS

This application is a third Divisional Application of U.S. patent application Ser. No. 14/213,502, filed Mar. 14, 2014, which is a Continuation-In-Part of U.S. patent application Ser. No. 12/712,040 filed on Feb. 24, 2010 entitled "Fission Meter and Neutron Detection Using Poisson Distribution Comparison," now U.S. Pat. No. 8,891,720 issued on Nov. 18, 2014, which is a Continuation-In-Part of U.S. patent application Ser. No. 11/233,228, filed on Sep. 21, 2005 entitled "Fission Meter," now U.S. Pat. No. 8,155,258 issued on Apr. 10, 2012, which in turn claims the benefit of U.S. Provisional Patent Application No. 60/612,968 filed by Mark S. Rowland and Neal J. Snyderman Sep. 24, 2004 and titled "Fission Meter." U.S. Provisional Patent Application No. 60/612,968 is incorporated herein by this reference.

STATEMENT REGARDING FEDERALLY SPONSORED RESEARCH

The United States Government has rights in this invention pursuant to Contract No. DE-AC52-07NA27344 between the United States Department of Energy and Lawrence Livermore National Security, LLC.

FIELD

The present invention relates to nuclear fission and more particularly to a system for accelerating detection of fissile material.

BACKGROUND

The detection and interdiction of illicitly trafficked Special Nuclear Material (SNM) is very important in the ongoing anti-terrorist activities undertaken by homeland security agencies. U.S. Patent Application No. 2005/0105665 by Lee Grodzins and Peter Rothschild for a system of detection of neutrons and sources of radioactive material, published May 19, 2005, provides the following state of technology information: "There is a need to find sources of radiation and other nuclear material that are clandestinely transported across national boundaries. The sources of clandestine nuclear material may be in the form of "dirty bombs" (e.g., a conventional explosive combined with radioactive nuclides designed to spread radioactive contamination upon detonation), fissile material, and other neutron and radiation emitting sources that may present a hazard to the public. During recent years, the United States government has placed mobile vehicles at strategic areas with gamma ray detectors dedicated to the task of finding fissile material. Atomic explosives may be made from $^{235}$U, a rare, naturally occurring, isotope of uranium that lives almost $10^9$ years, or $^{239}$Pu, a reactor-made isotope that lives more than $10^4$ years. $^{235}$U decays with the emission of gamma ray photons (also referred to as 'gammas'), principally at 185.6 keV and 205.3 keV. $^{239}$Pu emits a number of gamma rays when it decays, the principal ones being at 375 keV and 413.7 keV. These gamma rays are unique signatures for the respective isotopes. But fissile material invariably contains other radioactive isotopes besides those essential for nuclear explosives. For example, weapons grade uranium may contain as little as 20% $^{235}$U; the rest of the uranium consists of other isotopes. The other uranium and plutonium isotopes reveal their presence by gamma rays emitted by their daughters. For example, a daughter of $^{238}$U emits a high energy gamma ray at 1,001 keV; a daughter of $^{232}$U, an isotope present in fissile material made in the former USSR, emits a very penetrating gamma ray at 2,614 keV; and a daughter of $^{241}$Pu emits gamma rays of 662.4 keV and 722.5 keV."

U.S. Pat. No. 4,201,912 issued May 6, 1980 to Michael L. Evans et al. and assigned to the United States of America as represented by the U.S. Department of Energy, provides the following state of technology information: "A device for detecting fissionable material such as uranium in low concentrations by interrogating with photoneutrons at energy levels below 500 keV, and typically about 26 keV. Induced fast neutrons having energies above 500 keV by the interrogated fissionable material are detected by a liquid scintillator or recoil proportional counter, which is sensitive to the induced fast neutrons. Since the induced fast neutrons are proportional to the concentration of fissionable material, detection of induced fast neutrons indicates concentration of the fissionable material."

U.S. Pat. No. 3,456,113 issued Jul. 15, 1969 to G. Robert Keepin and assigned to the United States of America as represented by the U.S. Atomic Energy Commission, provides the following state of technology information: "An apparatus and method of detecting, identifying and quantitatively analyzing the individual isotopes in unknown mixtures of fissionable materials. A neutron source irradiates the unknown mixture and the kinetic behavior of the delayed neutron activity from the system is analyzed with a neutron detector and time analyzer. From the known delayed neutron response of the individual fission species it is possible to determine the composition of the unknown mixture. Analysis of the kinetic response may be accomplished by a simple on-line computer enabling direct readout of isotopic assay."

Traditional neutron detectors that have been used to augment gamma-ray detection systems typically rely on "gross-counting" to detect an increased neutron presence that may provide an indication of elevated fission from an unknown source. Fissile material detection with passive neutron multiplicity counters use the observation of correlated neutrons to indicate presence of fissile sources as opposed to industrial neutron sources (e.g., AmLi or AmBe). When measuring uranium, the spontaneous fission rate that is produced requires a passive measurement on the order of one day to see a correlated fission signal. To speed this process, an external neutron source or generator may be used to induce fission in the U235. Long-lived neutron sources like AmLi may induce fission and work well when the detection mechanism uses a Poisson discrimination technique as described herein. For enhanced operator safety, electrically generated neutron sources, commonly available in the form of DD (deuterium-deuterium) or DT (deuterium-tritium) sources are used. These generators are neutron source devices that contain compact linear accelerators and that produce neutrons by fusing isotopes of hydrogen together. The fusion reactions take place in these devices by accelerating the deuterium, tritium, or a mixture of these two isotopes into a metal hydride target, which also contains deuterium and/or tritium.

These electric neutron sources are intended to be either pulsed or steady state in neutron production. Electric neutron sources are regularly used to induce fission, where the user irradiates a sample and then looks for delayed neutrons as a signal that fissile material is present. However, such an approach is relatively hazardous and inefficient because of the high neutron intensity necessary to induce enough residual delayed fission product activity. A more efficient alternative to observing the delayed neutron fraction is to look for neutrons produced while the interrogation beam is on. This is more efficient because the induced fission rate is controlled by the fission cross section, unlike the delay-based method which delivers a few percent of this induced fission. This requires the detector to distinguish between the electric source neutrons and the induced fission neutrons, which has traditionally been impractical with present portable DD or DT electric neutron sources.

What is needed, therefore, is a method of distinguishing between these two types of detected neutrons by recognizing patterns of neutrons created and/or counted by the system.

Another disadvantage associated with present systems is that the electric generators used in such systems are almost always made using AC rectifying, high voltage DC power supplies. This introduces the problematic effect of electrical ripple on the DC supply that can cause correlation of neutron product, thus introducing unwanted correlation in the DD or DT neutron generator.

What is further needed, therefore, is a Poisson neutron source for use in in-beam interrogation systems that imposes virtually no ripple to distort the correlation of generated neutrons in a neutron detection system.

SUMMARY

Embodiments of the present invention provide a neutron detection system that can be used to discriminate fissile material from non-fissile material. In general, a fissile material is one that is capable of sustaining a chain reaction of nuclear fission. The detection system comprises a low cost digital data acquisition unit that collects data at high rate and processes in real-time, large volumes of data directly into information that a first responder can use to discriminate potentially radioactive materials. The detection system includes a Poisson neutron generator for in-beam interrogation of a possible fissile neutron source. The source is designed to have a DC power supply that exhibits electrical ripple on the order of less than one part per million. Certain voltage multiplier circuits are used to enhance the effective of series resistor-inductor circuits components to reduce the ripple associated with traditional AC rectified, high voltage DC power supplies.

To overcome the above-stated disadvantages of present systems, multiplicity counting objectives and counter functions have been incorporated with certain neutron sources and counting methods to distinguish between source neutrons versus induced fission neutrons. In general, the methods described herein are based on recognizing patterns of neutrons created and/or counted by the system. The patterns include detectable correlation that occurs on the time scales of nanoseconds or microseconds, which may be achieved with scintillators or gas detectors. Detection is therefore based on recognizing the count distribution correlation signature shape, and recognizing the rate at which the correlation arrives. These steps may be used in any method combination to meet detection requirements. For example, embodiments utilize the fact that the AmLi type neutron source is distinguished by the fact that the neutron output rate is Poisson, which enables a multiplicity counter to distinguish fission neutrons, which are correlated.

In the following description, numerous specific details are introduced to provide a thorough understanding of, and enabling description for embodiments of the neutron detection system. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

A standard approach to locating neutron sources is to use a neutron detector to look for count rate increases above background patterns. Given the number of legitimate neutron sources used in industry, deploying standard neutron detectors will result in a large number of alarms that will need to be resolved by more intrusive inspections. Embodiments of the present invention provide a simple way to discriminate the commonly used neutron sources from illicit (fissile) neutron sources. This technique functions in a passive mode much like a standard portal monitor. Embodiments also provide a system for converting the technique to an active interrogation scheme.

Embodiments of the system identify when fission is occurring by providing an analysis of the range of simultaneous neutrons. Fission is defined as the emission of multiple neutrons after an unstable nucleus disintegrates. For example, Pu240 decays at a rate of about 400 fissions per second per gram of Pu240 atoms. When the fission occurs, multiple neutrons are emitted simultaneously, with the number ranging from zero to eight neutrons. This simultaneous neutron emission characteristic is unique to fission. Depending on the multiplication from the mass of fissionable material, the knock-on fission chain time evolution can easily last into the millisecond time scale.

Embodiments provide a method of identifying fission from an unknown source. The method comprises the steps of counting neutrons from the unknown source and detecting excess grouped neutrons, over some time interval longer than cosmic detections, to identify fission in the unknown source. In one embodiment, the step of detecting excess grouped neutrons includes plotting a Poisson count distribution on top of a measured count distribution, such that the mean count of the data is the same as that of the Poisson curve, and discerning differences attributed to fission in the unknown source.

A fission meter apparatus for identifying fission from an unknown source is also described. The fission meter apparatus comprises a multiplicity counter that looks for a range of excess neutrons from the unknown source, a neutron detector operatively connected to the multiplicity counter, and a calculating system operatively connected to the neutron detector that is set up to compute a difference between actual and expected neutron group sizes, which then positively identifies fission in the unknown source. In one embodiment, the calculating system is a system for plotting a Poisson count distribution superimposed over a measured count distribution, such that the mean count of the data is the same as that of the Poisson curve. The apparatus includes a graphing component that displays the plot of the neutron distribution from the unknown source over a Poisson distribution and a plot of neutrons due to background or environmental sources. A known neutron source can be placed in proximity to the unknown source to actively interrogate the unknown source in order to accentuate differences in neutron emission from the unknown source from Poisson distributions and/or environmental sources.

Although the described embodiments are susceptible to modifications and alternative forms, specific embodiments are shown by way of example, and it should be noted that the invention is not limited to the particular forms disclosed. The described embodiments cover all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

INCORPORATION BY REFERENCE

Figure 1:
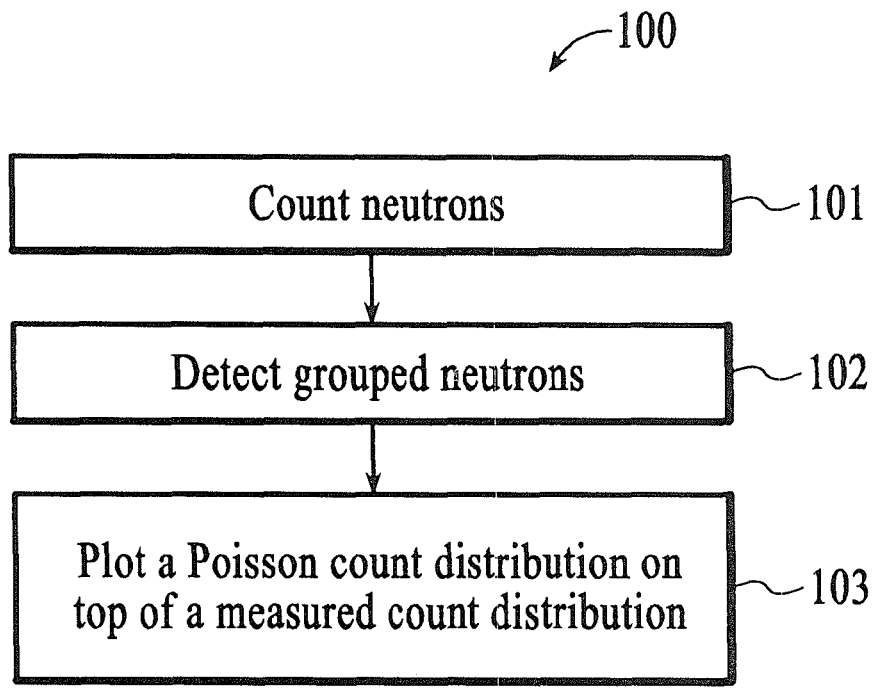
FIG. 1 illustrates a method of detecting fission from unknown and potentially dangerous sources of nuclear radiation, under an embodiment.

Each publication, patent, and/or patent application mentioned in this specification are herein incorporated by reference in its entirety to the same extent as if each individual publication and/or patent application was specifically and individually indicated to be incorporated by reference.

Among other references specifically cited herein, U.S. patent application Ser. No. 12/712,040, filed on Feb. 24, 2010, U.S. patent application Ser. No. 11/233,228, filed on Sep. 21, 2005, and U.S. Provisional Patent Application No. 60/612,968 filed Sep. 24, 2004 are hereby incorporated in their entirety by reference.

DETAILED DESCRIPTION OF THE INVENTION

Referring to the drawings, to the following detailed description, and to incorporated materials, detailed information about the invention is provided including the description of specific embodiments. The detailed description serves to explain the principles of such embodiments, which are susceptible to modifications and alternative forms. The described embodiments are not limited to the particular forms disclosed. The invention covers all modifications, equivalents, and alternatives falling within the spirit and scope of the invention as defined by the claims.

FIG. 1 illustrates a method of detecting fission from unknown and potentially dangerous sources of nuclear radiation, under an embodiment. A system implementing the method first counts neutrons emitted from the source; block 101. It then detects grouped neutrons, block 102, and plots a Poisson count distribution on top of a measured count distribution, block 103. Evident is the opportunity to log the time scale for the set of correlated neutrons that are counted.

An embodiment of the system 100 comprises plotting a Poisson count distribution over a measured count distribution, such that the mean count of the data is the same as that of the Poisson curve. The difference between the two superimposed distributions (curves) is then analyzed to discern neutron emission that may be attributed solely to fission in the unknown source.

A Poisson distribution or curve is a discrete probability distribution that expresses the probability of a number of events occurring in a fixed period of time if these events occur at a known average rate and are independent of one another. The Poisson distribution formula is as follows: $f(k;\lambda)=(e^{-\lambda}\lambda^{k}/k!)$ where k is the number of occurrences of an event and $\lambda$ is a positive real number of the expected number of occurrences during the given interval.

The system implementing the method of FIG. 1 can be used for mobile or stationary monitoring and characterization of the type of neutron sources inside packages. Some examples of uses of the system 100 include inspection of packed cargo containers and trucks. The present invention can be used for preventing illicit trafficking of fissioning nuclear material, can be used for the management of inventories of nuclear material, and can be used for management of waste streams of nuclear material. The system 100 is particularly useful where the desire is to have a simple, quick approach that minimally trained operators can use to improve the control of fissioning material.

In physics, fission is defined as the emission of multiple neutrons after an unstable nucleus disintegrates. For example, Pu240 decays at a rate of about 400 fissions per second per gram of Pu240 atoms. When the fission occurs, multiple neutrons are emitted simultaneously, with the number ranging from zero to eight neutrons. The present invention provides a system that can be used to identify when fission occurs by looking for the range of simultaneous neutrons. This simultaneous neutron emission characteristic is unique to fission. Embodiments are directed to a system that includes a multiplicity counter and a neutron detector that is set up to observe the presence of time grouped neutrons in order to detect the simultaneous emission of neutrons.

The method and system corresponding to that illustrated in FIG. 1 has many uses. For example, one use of the method comprises preventing illicit trafficking of fissioning nuclear material. Another use of the method comprises management of inventories of nuclear material. Another use of the method comprises management of waste streams of nuclear material. The method and system of FIG. 1 is particularly useful where the desire is to have a simple, quick approach that minimally trained operators can use to improve the control of fissioning material. The operators, for example may include border or traffic police, baggage handlers or freight companies, or for international treaty agreements that endeavor to identify, segregate, or manage the world's inventories of nuclear material.

Figure 2:
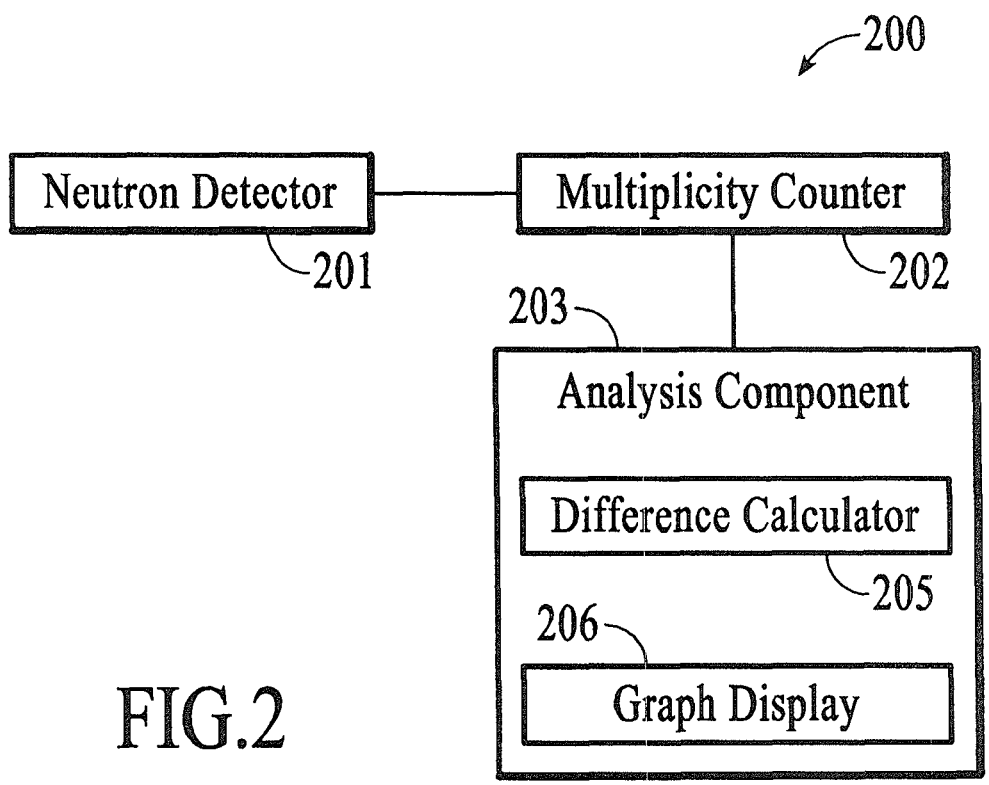
FIG. 2 illustrates a system for detecting fission from unknown and potentially dangerous sources of nuclear radiation, under an embodiment.

Referring now to FIG. 2, another embodiment of a system constructed in accordance with the present invention is illustrated. This embodiment of the system is designated generally by the reference numeral 200. The system 200 comprises a number of interconnected the structural components. A neutron detector 201 detects neutrons, a multiplicity counter 201 looks for a range of simultaneous neutrons from the unknown source. A calculator 203 calculates the difference between a Poisson distribution and an unknown distribution. The neutron detector 201 is operatively connected to the multiplicity counter 202. The calculator 203 is operatively connected to the multiplicity counter 202 and is set up to see time grouped neutrons to see simultaneous neutrons and identify fission from the unknown source.

The system 200 provides a simple way to discriminate the commonly used neutron sources from illicit (fissile) neutron sources. The system 200 comprises a fission meter apparatus for identifying fission from an unknown source. The fission meter apparatus 200 comprises a multiplicity counter 202 that looks for a range of excess neutrons from the unknown source, a neutron detector 201 operatively connected to the multiplicity counter, and a calculating system or analysis component 203 operatively connected to the multiplicity counter 202 that includes a difference calculator 205 to compute a difference between actual and expected neutron group sizes, which when positively identifies fission in the unknown source. In one embodiment, the analysis component 203 also includes a graph display component for plotting a Poisson count distribution and graphically displaying it as superimposed on a measured count distribution, such that the mean count of the data is the same as that of the Poisson curve.

In one embodiment, the detector 201 is a neutron detector subsystem that consists of multiple moderated 7.5 atmosphere Helium-3 ($^3$He) neutron detectors. The detector subsystem includes high voltage supplies for the Helium tubes and preamplifier or discriminator units required to achieve the pick-off (timing) of the neutron events. Depending upon configuration, the detector may consist of two or more large (photodetectors or anode wire charge collectors) avalanche photodiodes viewing a gas volume filled with the pressurized Helium. Neutrons are detected through scintillation and ionization of the Helium.

A wavelength shifting process, such as that known to those of ordinary skill in the art, may be used to measure the degree of scintillation in order to provide a measure of neutron count in the photodiodes. Alternatively, the ionized He3 and a small amount of buffer gas like CO2 or Argon will ionize under the proton emission from neutron capture in He3. In a further alternative, the scintillation from neutron interactions in a volume of liquid scintillator common to the counting field may substitute for the scintillation in the gaseous active detector volume. The detector 201 gathers the neutron data and analyzes the data for coincidences, which are doublets, triplets, quads, or any multiplet up to a high order arriving over a logged time scale. Neutron multiplicities in various time sub-gates (the time scale indicator) during each data acquisition cycles are recorded. An acquisition cycle may be defined as 512 time bins. The multiplicity counter 202 may comprise an electronic subsystem that processes the count data from the detection system. The relative time intervals between neutrons arriving at the detector are measured to build a statistical distribution of the multiplicity of the neutron detection.

In one embodiment, the multiplicity counter takes each detected neutron and looks in up to 512 time interval gates to record the time interval between each neutron and others in the data stream from the detector. From the same data stream the shorter time intervals (e.g., on a nanosecond time scale) carry information unique to cosmic spallation induced neutrons. The time bins define counting gates that are triggered by a trigger conditions. The trigger condition may be the detection of a first neutron. The detection of additional neutrons after the trigger neutron and within the longer time bins constitutes a pair, or more, of observed neutrons.

As further shown in FIG. 2, the analysis component 203 includes a difference calculator that analyzes the output from the multiplicity counter to determine if it is consistent with a background noise, an innocent source, or a potentially dangerous radioactive source. The analysis component 203 includes a difference calculator 205, which calculates the difference between the unknown source and a standard Poisson distribution, and a graph display that displays the neutron emission distribution of the unknown source and the Poisson distribution in a superimposed graphical representation. In one embodiment, the analysis component 203 performs an analysis of the neutron multiplicity data through a Feynman Variance Technique, or equivalent method.

In one embodiment of the system 200, the analysis component 203 includes a plotting system for plotting a Poisson count distribution on top of a measured count distribution, such that the mean count of the data is the same as that of the Poisson curve. In an embodiment, the plotting system 203 is a computer. The system 200 provides a neutron detector that can be used to discriminate fissile material from non-fissile material. It comprises a low-cost digital data acquisition unit that collects data at high rate, and in real-time processes large volumes of data directly into information that a first responder can use to discriminate various types of materials.

Neutron Count Plots

One significant characteristic of fission is that neutrons emit in groups. Random sources of neutrons are emitted with no regard for grouping, however, since the appearance of these neutrons at the detector are randomly spread in time, some may accidentally appear in close temporal proximity. An example is a neutron detector that counts neutrons for short periods of time, for example ½ millisecond time periods (gate periods). This example time corresponds to a typical neutron diffusion time in a typical moderated detector, the choice of which depends on specifics related to detector design. If the ½ millisecond period is counted once, the count may be one, two, or three counts, or some other integer number, including zero. It is desirable to select an appropriate observation time, such as two to three times the typical neutron diffusion time, and then repeat the sampling of counts period many times to produce a histogram of counts described as the number of occurrences of each multiplet group. This yields a distribution of the number of times (e.g., 0, 1, 2, 3) that neutrons were observed over a number of detection periods (e.g., 10,000 repeated periods). In the case of scintillation counters, these need not be moderated, and this may be preferred as appropriate to the counter system design, so that the nanosecond time scales of the time correlations may be differentiated from the longer fission chain evolution.

Figure 3A:
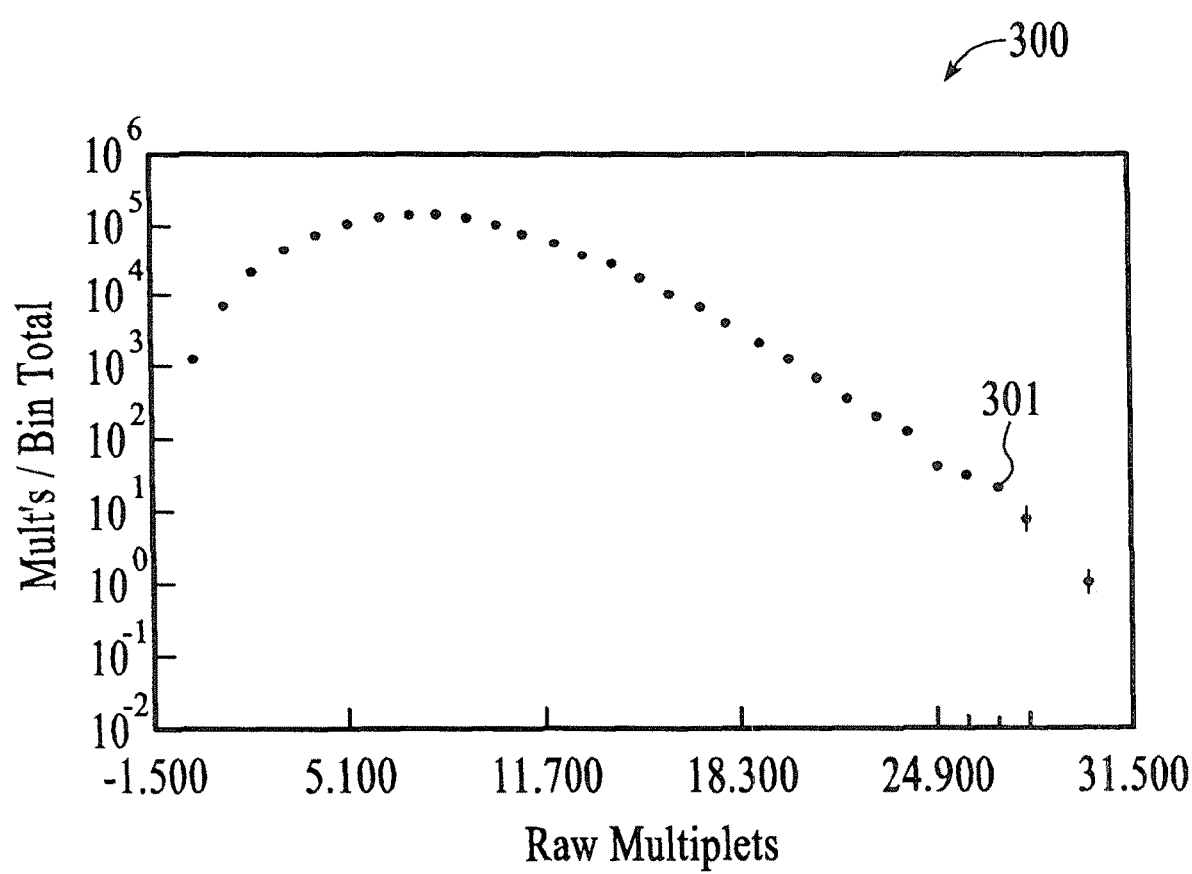
FIG. 3A illustrates an example plot of the count distribution of the frequency of neutrons emitted from an unknown source counted in a defined duration count gate.

FIG. 3A illustrates an example plot of the count distribution of the frequency of neutrons from an unknown source counted in a 512 microsecond count gate. For the example plot 301 of FIG. 3A, it can be seen that eight neutrons were observed $10^5$ times and 25 neutrons were observed about 100 times. The observed plot 301 provides an indication of the detection of coincidental neutrons (e.g., two or more neutrons emitted within a defined time period after detection of the first neutron) during a particular time gate.

Fission is unique in that it creates real correlations, while non-fission neutron sources create accidental correlations. Embodiments provide a method and system that utilizes new developments in how fission neutron chains are modeled to simplify and remove problems related to the assay of unknown packages of fissioning material.

Counting neutrons by looking for time-correlated groupings is called multiplicity counting. The groupings arise from the fission process where a portion of a fission chain is detected. The analysis of this type of data assists in deriving mass, multiplication, detector efficiency, and alpha ratio (mMeA). Other factors in the analysis include neutron lifetime (L=1/λ), measurement gate width (T), the maximum size of neutron multiplets observed (n), the background correlation and count rate (B), and the generalized Poisson exponent (A).

Figure 3B:
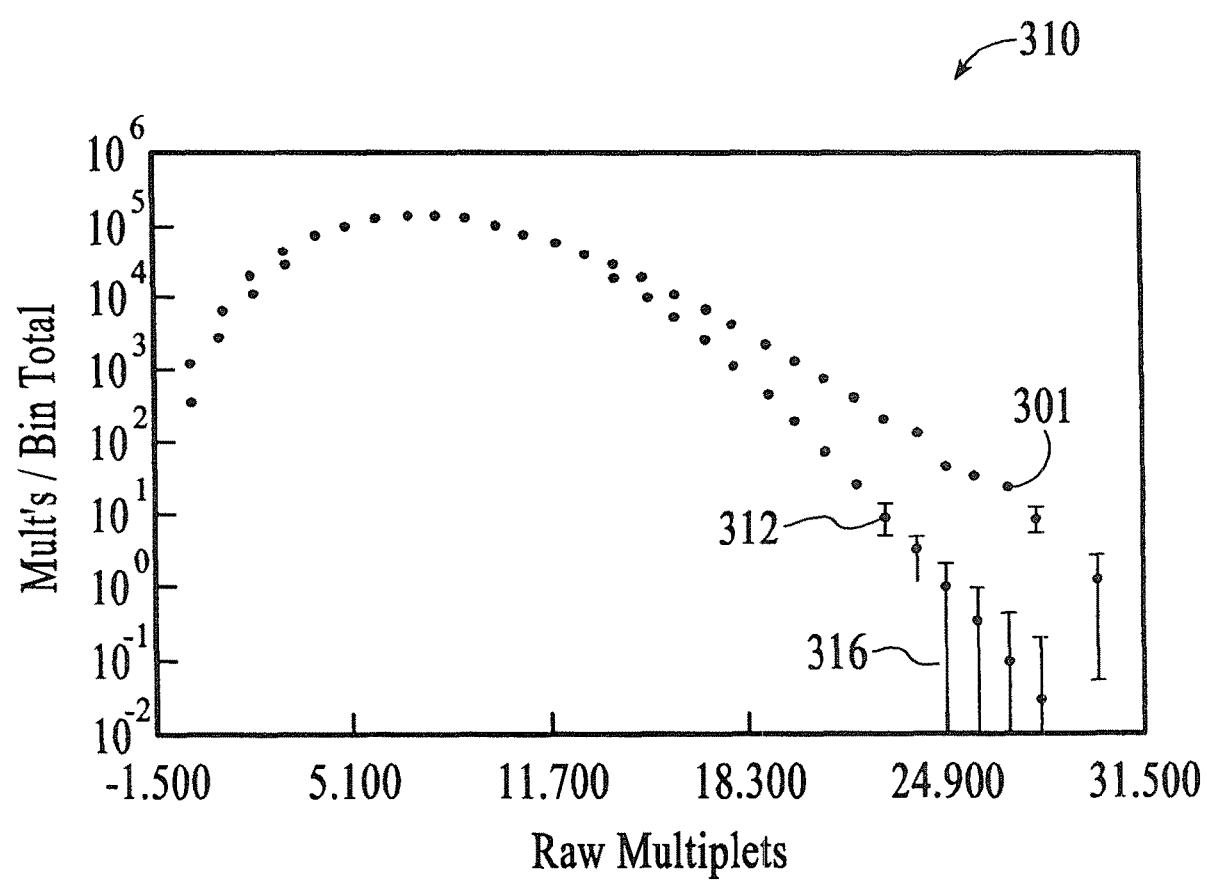
FIG. 3B shows a plot of a Poisson count distribution on top of the measured count distribution.

Referring now to FIG. 3B, a plot further illustrates the embodiments 100 and 200. The plot is designated generally by the reference numeral 310. The top curve 301 is a count distribution of the frequency of neutrons from an unknown source counted in a 512 microsecond count gate, such as that illustrated in FIG. 3A. Correction for cosmic induced correlation is performed by selecting only the correlation time scales greater than tens of nanoseconds. For example, eight neutrons were observed $10^5$ times and 25 neutrons were observed about 100 times. The bottom curve 312 is a Poisson count distribution with the same mean count i.e., about seven. As can be seen in FIG. 3B, there is an increase in frequency of data above the Poisson points. That is, the actual distribution curve 301 exhibits a greater number of observed neutrons above the mean count than does the Poisson curve 312. This represents an excess number of emitted neutrons from the unknown source over the statistically expected number represented by the Poisson curve 312. If an operator observes such an excess, either visually or via a numerical subtraction, then fission is identified.

The actual amount of excess that triggers the detection of fission is defined by the constraints of the system and normal operating practice. The error bars 316 represent a range of error assigned to each count. If the actual number of neutrons exceeds the Poisson number but is within the error range, then fission may not be cause of such excess. However, if the actual number of neutrons exceeds the error range of the Poisson count by a pre-defined amount, then such an excess may be attributed to fission.

In general, the presence of background radiation (e.g., cosmic rays) may be a factor in any detection process. However, methods of the fission meter plot described herein are still useful and generally not overwhelmed by background effects. In certain cases, a very weak fission source may be overwhelmed by combinations of background noise, however, a fission source that is practically detectable will have a count distribution curve that is similar to the Poisson distribution, as shown in FIG. 3B. Embodiments include a method for distinguishing background radiation to further refine the detection of fissioning material. Background radiation may be correlated to some degree, but has a very distinct count distribution curve. It has a flattened out portion after a certain number of counts, and does not monotonically decrease, as does a Poisson distribution.

Figure 3C:
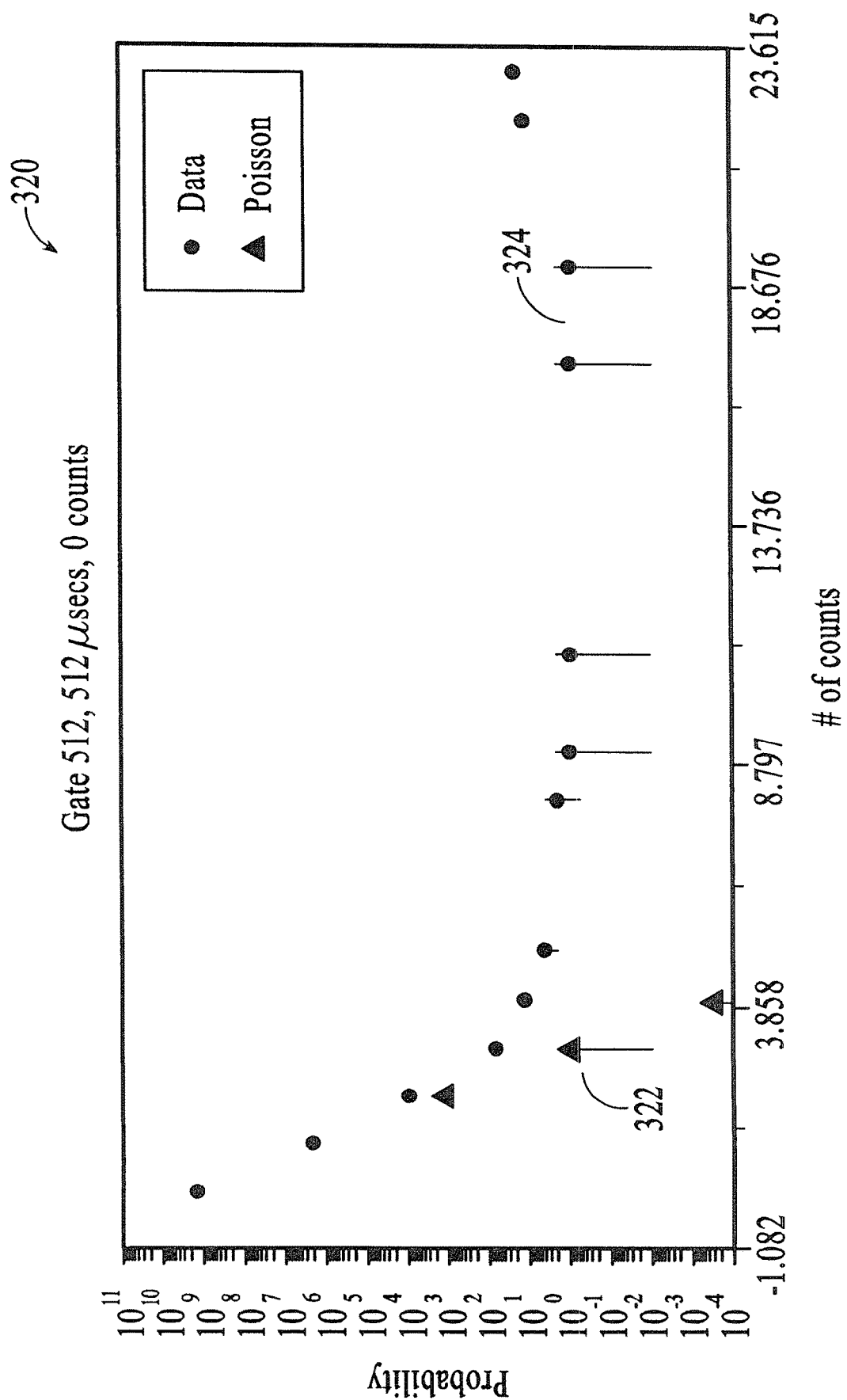
FIG. 3C shows a plot of a Poisson count distribution compared to background radiation.

FIG. 3C shows a plot of a Poisson count distribution compared to background radiation. As shown in FIG. 3C, a count distribution for observed background data 324 is plotted relative to a Poisson distribution 322. A pure background source will show a curve that flattens or has a kink shape around counts 3 or 4, as shown in FIG. 3C. Therefore, a detectable radiation source will have a count distribution that resembles the Poisson shape, but with no kink, and depending on its strength, it will overwhelm the background effects in the 3 and 4 count region. The practical range of filtering out background depends on various parameters associated in specifying a neutron detector, such as efficiency, distance from source, and so on. In a typical application, background count rates may be on the order of 3.5 counts/second (cps). A Cf (Californium) fission source with Multiplication=1 typically makes one million neutrons per second; at a distance of one meter, the detector efficiency is around 1% so the count rate would be thousands of cps. Such an example overwhelms the background effects. For a significant amount of fissioning material (e.g., tens of kilograms of uranium), for which the Multiplication=10, at one meter the count rate is 3 cps so the total count rate would be 6.5 cps. There is a clear deviation of 3, 4, 5 counts because of the multiplication, and the higher multiplets overwhelm background even though the count rate is near background. Through the graph display process 206, the generated count distribution plots will show that there is no "flat" portion on the tail on the observed count plots, unlike the background data shown in FIG. 3C. Thus, this method provides a means of distinguishing true fissioning sources from mere background and provides a basis for comparing a non-background source with a Poisson distribution. For cases in which the detector is within range of a signal from a fissioning source, it will report a distinction from both Poisson and background correlation.

While cosmic induced spallation neutrons can be counted and appear as correlated, they occur in a time scale that can be simply segregated form the longer fission chains of interest. In the case of a spallation neutron causing a legitimate fission chain in the hypothetical mass of nuclear material, this will generate a legitimate fission chain worthy of detection since it is a valid signature of the desired object.

The method and systems 100 and 200 comprise a first step of counting neutrons from the unknown source and a second step of detecting excess grouped neutrons to identify fission in the unknown source. In another embodiment the method and systems 100 and 200 comprise the steps of counting neutrons from the unknown source and detecting excess grouped neutrons to identify fission in the unknown source wherein said step of detecting excess grouped neutrons to identify fission in the unknown source includes plotting a Poisson count distribution on top of a measured count distribution, such that the mean count of the data is the same as that of the Poisson curve, and discerning differences attributed to fission in the unknown source. In another embodiment the method and system 100 and 200 comprise the steps of counting neutrons from the unknown source and detecting excess grouped neutrons to identify fission in the unknown source includes plotting a Poisson count distribution on top of a measured count distribution, such that the mean count of the data is the same as that of the Poisson curve, and discerning differences attributed to fission in the unknown source and wherein said step of discerning differences attributed to fission in the unknown source comprises discerning visible differences in said Poisson count distribution superimposed over a measured count distribution plot that are attributed to fission in the unknown source.

The process illustrated in FIG. 3B of plotting the multiplet structure of the Poisson distribution and comparing it in a multiplet-by-multiplet fashion with the observed distribution is unbiased by any expectation that the triggering event (e.g., a trigger neutron) is the correct neutron with regard to whether it is a real or accidental. This automatically alerts the user to the correct and exact expected rate of accidental multiplets greater than one, and prevents the problem caused by systems that assume that all counts within the A gate are accidentals, which leads to the possible rejection of valid correlation information.

In general, neutrons are used in many industrial applications. Neutron signatures also indicate the presence of fissioning nuclear material. It is desirable to be able to separate benign industrial neutron sources from fission sources. Traditionally, detection of nuclear material has been accomplished by neutron counting. If neutron sources were rare, the misinterpretation of any neutron source as a fission source would be of little consequence. However, with the large-scale introduction of nuclear monitoring equipment in daily commerce comes the need to not confuse the traffic of industrial sources with illicit traffic. The method and systems 100 and 200 provide the basis for a visual or automated comparison of raw count distribution data, to a Poisson distribution with the same mean count, to show graphically the intuitive sense that the characteristic of fission is present. Optimally, the excess correlation, above a Poisson rate of correlation, may be alternatively or additionally provided by observing that numerical characteristics of the data and the corresponding Poisson distribution may be computed to form a numerical difference, redundantly indicative of fission.

As stated above, the characteristic of fission is that neutrons emit in groups. That is, potentially dangerous unknown sources emit multiple coincident neutrons. This simultaneous emission is used in the detector system described herein to distinguish from random sources of neutrons that are emitted with no regard for grouping; however, since the appearance of these neutrons at the detector are randomly spread in time, some may accidentally appear in close temporal proximity. Fission is unique in that it creates real correlations, while non-fission neutron sources create accidental correlations. Unrecognized is the relative histogram comparison of the measured or unknown neutron source, with a mathematically generated count histogram that represents the hypothetical case of no fission. Visually, in isolation, one histogram looks like another. FIG. 3B illustrates a detector system that includes a histogram display system that allows direct graphical comparison of the measured source to the mathematically generated or Poisson distribution. The shape of the measured source histogram is derived from the characteristics of the measured unknown source. For the example of FIG. 3B, the tail portion of the histogram 301 is above the random or Poisson histogram 312. This excess correlation is due to fission, illustrating that a simple plot of data collected in one measurement, can be analyzed with a relatively simple procedure involving straightforward observation and comparison. Alternatively, it is possible to compute various quantities in order to derive mathematical count differences between the histograms in order to obtain numeric measures of excessive neutron emission. Threshold values can be defined such that automated processes can indicate the presence of a potentially dangerous source if the difference between the measured count exceeds the Poisson count in excess of the threshold.

One example of an alternative embodiment to the histogram overplot concept is to numerically compute quantities based on the single measurement of an unknown. Conceptually, the objective is to realize that the differences apparent in a comparison of histograms may be described as the number of pairs of counts observed in the unknown minus the number of count pairs expected if there were no fission (but the neutrons came from a non-fissioning neutron source). This can be expressed as:

# of pairs observed−expected random # of pairs

If the difference is zero, then the observed neutron source is not undergoing neutron fission. The number of pairs is only one example of a statistical quantity derivable from the measured histogram. Others might be the third or fourth moment of the histogram.

An alternative embodiment to the graphical histogram approach involves an analysis of the number of pairs of neutrons. As stated above, pairs of neutrons in excess of those expected is the test. Numerically this may be computed from the measured histogram:

$$\sum_{n=0}^{\infty} \frac{\frac{n(n-1)}{2}}{2\sum_{n=0}^{\infty} Cn} Cn - \left(\frac{\sum_{n=0}^{\infty} nCn}{\sum_{n=0}^{\infty} Cn}\right)^2 \cdot \frac{1}{2}$$

This difference represents the absolute number of pairs in excess of that expected from a non-fissioning neutron source. In the above equation, n is the x-axis of the histogram and is the size of the group of neutrons observed, and Cn is the number of times that a group of n neutrons was observed after repeating the ½ msec. measurement a large number of times. Note that the mean count of the measured histogram defines the histogram of the expected or hypothetical non-fission histogram. The mean count of the measurement is:

$$c\text{-bar} = \overline{c} = \frac{\sum_{n=0}^{\infty} nCn}{\sum_{n=0}^{\infty} Cn}$$

The histogram expected from a non-fission source will have the same C-bar, however the shape of the histogram will be described by:

$$Cn\text{-poisson} = \frac{\overline{c}^n}{n!} e^{-\overline{c}}$$

In the above equation, n is the count group size. Whether the system simply plots Cn-Poisson on top of the measurement, as in the first embodiment, or computes difference quantities, as in the second embodiment, they represent the same insight that a uniquely observable fission neutron signature can be created from a single measurement, and can be useable by minimally trained operators to separate high value objects from common industrial sources.

Figure 4:
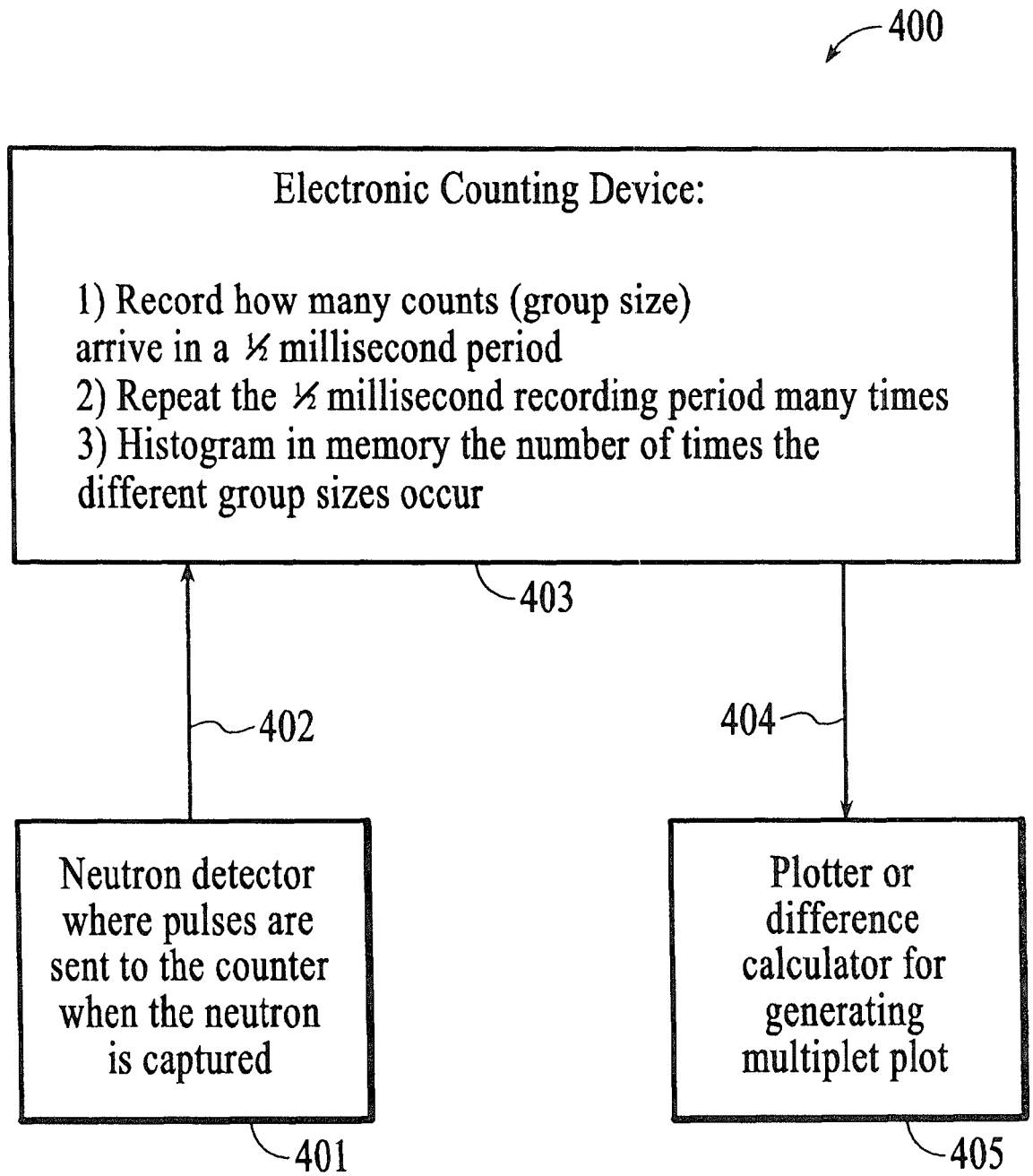
FIG. 4 illustrates another embodiment of a system constructed in accordance with the present invention.

Referring now to FIG. 4, another embodiment of a system constructed in accordance with the present invention is illustrated. This embodiment of the system is designated generally by the reference numeral 400. The neutron detector 401 detects neutrons. The neutron detector 401 is operatively connected to a counter 403. The arrow 402 illustrates pulses sent from the detector 401 to the counter 403. Pulses are sent to the counter 403 when neutrons are captured.

The counter 402 and is set up to see time grouped neutrons to see simultaneous neutrons and identify fission from the unknown source. The counter 402 (1) can record how many counts (group size) arrive in a ½ millisecond period, (2) repeat the ½ millisecond recording period many times, and (3) plot a histogram of the number of times the different group sizes occur.

The counter 403 is operatively connected to a plotter or difference calculator 405. The arrow 402 illustrates information from the counter 403 being sent the plotter or difference calculator 405. The system 400 provides a simple way to discriminate the commonly used neutron sources from illicit (fissile) neutron sources. In one embodiment, a system plots a Poisson count distribution on top of a measured count distribution, such that the mean count of the data is the same as that of the Poisson curve. Such a comparison plot is shown in FIG. 3B.

In one embodiment, the neutron detector is used in a portable neutron source identification system that helps detect the presence of illicit radioactive material for use in homeland security applications. Such material can be used in deadly terrorist weapons such as Improvised Nuclear Devices (IND) or state built nuclear weapons. In general, these weapons require the presence of a so-called Special Nuclear Material (SNM), that is, Uranium or Plutonium, to create a nuclear explosion. Traditional methods of detecting and identifying the presence of SNM involve the use of gamma-ray detection. These methods, however, can be defeated through the use of heavy metal shielding. The neutron detector according to embodiments augments the technique of gamma-ray detection by identifying fission neutron sources by examining the inherent characteristics of the neutron decay process. The neutron detector under embodiments includes processing and filtering components that not only count neutrons, but also check the source and environmental conditions for the existence of neutron sources beyond simple noise or environmental effects. Such a detector allows for the rapid and relatively certain detection of neutron sources from potentially dangerous sources, such as improvised nuclear devices or similar weapons.

A neutron source can be any of a variety devices that emit neutrons, irrespective of the mechanism used to produce the neutrons. Depending upon variables including the energy of the neutrons emitted by the source, the rate of neutrons emitted by the source, the size of the source, neutron source devices can be found in a diverse array of applications in areas of physics, engineering, medicine, nuclear weapons, petroleum exploration, biology, chemistry, nuclear power and other industries. Man-made sources include reactors that produce neutrons that can be used for experiments, and spallation sources that are high flux sources, in which protons that have been accelerated to high energies hit a target material, prompting the emission of neutrons.

Figures 5, 6:
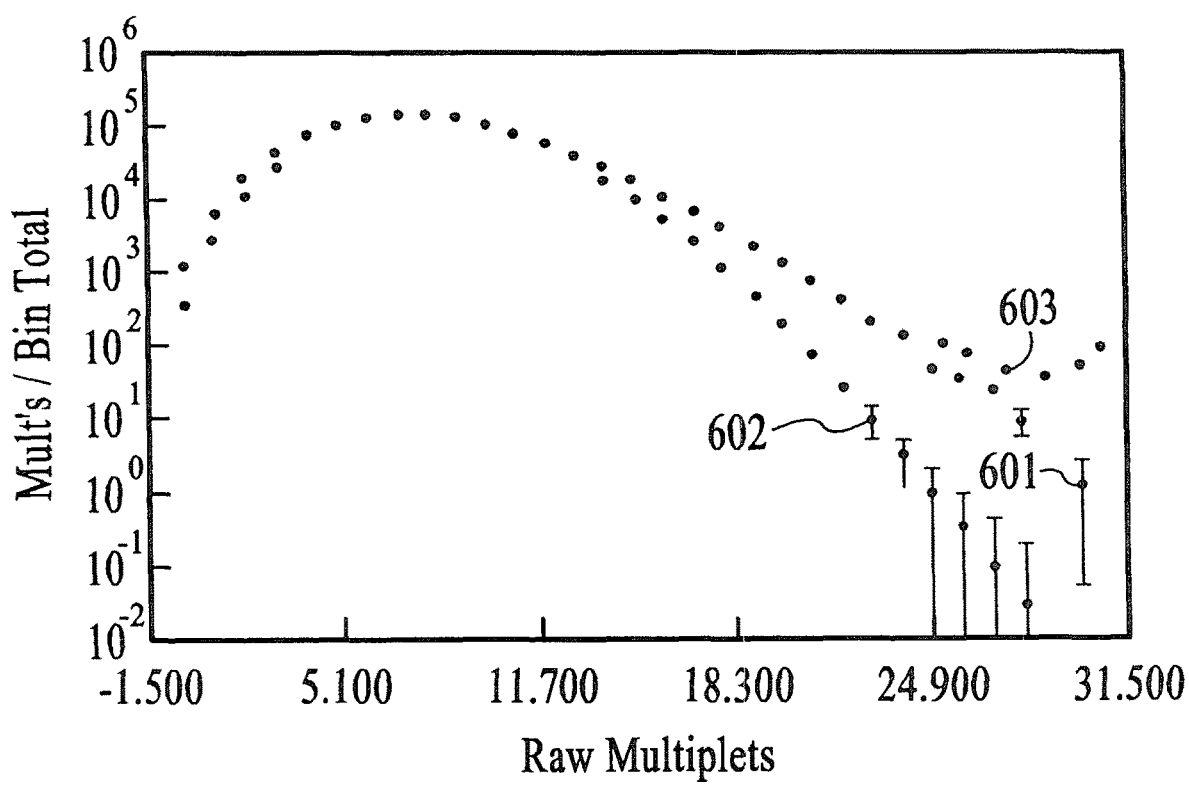
FIG. 5 is a table that illustrates a background count distribution.
FIG. 6 illustrates a neutron distribution curve illustrating a cosmic source.

In one embodiment, the neutron detection system includes a method for allowing the filtering of background neutron noise due to other sources, such as cosmic or man-made sources. Typical background consists of single neutrons and neutron groups from multiple neutron events caused by cosmic rays. The Poisson distribution of the events will cause some random coincidence events. These random coincidences can be calculated using the singles count rate and device characteristics. FIG. 5 is a table that illustrates a background count distribution for an example time period. For table 500 of FIG. 5, data was collected for a period of one hour resulting in a count of 8552 for a count rate of 2.31 counts per second (cps).

FIG. 6 illustrates a neutron distribution curve illustrating a cosmic source. In one embodiment, the simple observation of a neutron distribution curve with a shape like that shown in FIG. 3A would indicate the presence of neutrons due to cosmic interference. Correlation is indicated by the presence of events with higher order multiplicity in the distribution. As shown in FIG. 6 the actual background 603 is slightly more correlated than the neutron distribution from the unknown source 601, and both are more correlated than the pure Poisson distribution 602. Such an effect is also shown in FIG. 3C. As shown in FIG. 6, the actual background curve 603 has a characteristic and relatively pronounced curve up at the very end of the plot. The shape of curve 603 can be used by an analyst or a program to determine whether or not the presence of neutron emission is due to cosmic effects as opposed to a potentially dangerous source.

The distribution curves 601, 602, and 603 shown in FIG. 6 provide a graphical basis on which an analyst can view and identify man-made or environmental sources of neutrons. The difference in counts above the mean, that is, in the upper portion of each curve, along with the shape of the curve can be used to characterize the criticality of the hazard posed by an unknown source relative to the background and Poisson distributions. In one embodiment, analysis of the graphical neutron distribution data as generated by the neutron detection system can be viewed and analyzed by a human operator.

Alternatively, the graphical distribution data can be further processed in a program or electronic module to provide an interpretation of the data. This module can be configured to analyze one or more parameters associated with the distribution plot such as shape, rate of rise of a portion of the curve, point-by-point differences with the Poisson and/or environmental neutron plots, and so on. Such interpretation information can be used by a user or a further response system to trigger an appropriate response to the unknown source, such as sounding an alarm, ordering an evacuation, initiating an automatic detonation sequence, or any other appropriate action.

Figure 7:
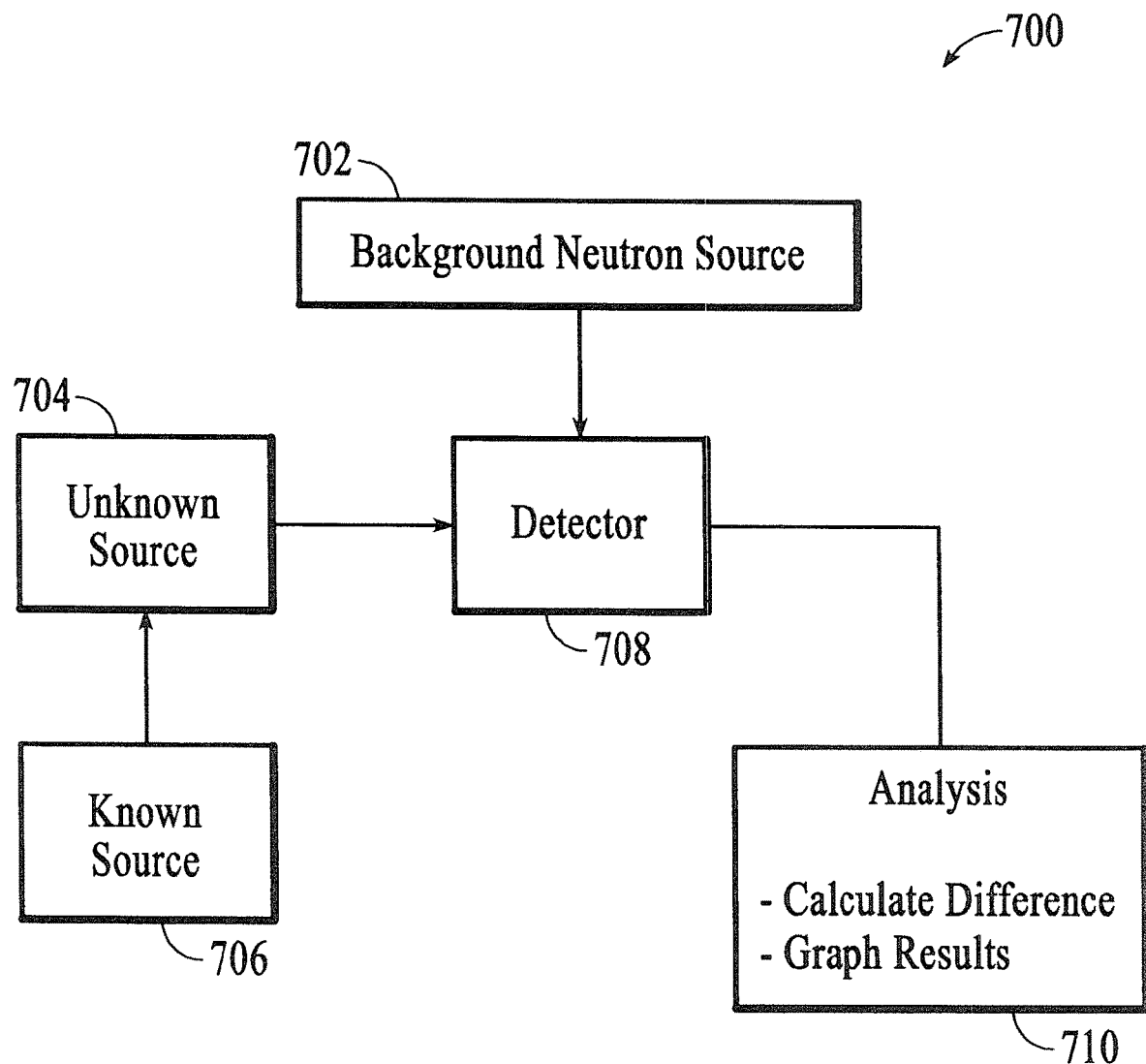
FIG. 7 illustrates a neutron detection system with active interrogation, under an embodiment.

In one embodiment, the detection system includes a module that allows for active interrogation of an unknown neutron source. This system includes a source of neutrons, such as Californium (Cf) or Americium-Beryllium (AmBe) placed at a known distance from the unknown source. The active interrogation due to the presence of a neutron source effectively forces neutrons into the source and results in more fissions. This generally increases the speed in which the neutron distribution for the unknown source is generated. The resulting neutron distribution is then observed. FIG. 7 illustrates a neutron detection system with active interrogation, under an embodiment. In system 700, unknown source 704 is placed in the proximity of detector 706. The detector 706 also picks up neutron emissions from background source 702. To counteract the effects of this background noise, a known source 708 is used to drive neutrons into the unknown source 704. The resulting neutron emission distribution is then plotted relative to a Poisson distribution, and a graph, such as that shown in FIG. 3 is displayed using graph generator 710. The active interrogation system of FIG. 7 can increase the strength of the unknown source above the ten to one ratio relative to the background, thus allowing greater possibility of detection from unnatural sources.

Accelerating—Fissile Material Detection

As described above, fissile material detection with a passive neutron multiplicity counter is relatively well-known, and the basic detection mechanism depends on the observation of correlated neutrons, where the counter will clearly show that fission creates correlated neutrons in contrast to an industrial neutron source (like AmLi or AmBe) that does not create correlated neutrons.

FIG. 3B illustrates the comparison of plots for an uncorrelated (Poisson) neutron source 312 with a correlated (observed) neutron source 301. The attribute that describes the uncorrelated data is that of a time-random neutron source, and is described by the Poisson probability distribution: $b_n=(C^n/n!)e^{-C}$. In this equation, b is the probability of detecting a particular number of neutrons, n, during a counting window (e.g., 512 microseconds), C is the average number of counts observed during the counting window. In the plots of FIG. 3B, the observed curve 301 is above Poisson curve 312 because the neutrons detected were created by a fission process, where fission neutrons are created simultaneously in groups ranging in size from zero to about eight neutrons. The groups of neutrons from fission are therefore also detected with groupings that favor the higher multiplets, as shown in FIG. 3B.

Neutron generators generally contain compact linear accelerators that produce neutrons by fusing isotopes of hydrogen together. A DD neutron source fuses deuterium atoms (D+D) to form an He-3 ion and a neutron with a kinetic energy of about 2.5 MeV. A DT neutron source fuses a deuterium and a tritium atom (D+T) to form an He-4 ion and a neutron with a kinetic energy of about 14.1 MeV. Neutrons are produced by accelerating Deuterium and/or Tritium ions into a hydride target loaded with Deuterium and/or Tritium. Deuterium atoms in the beam fuse with the DIT atoms in the target to produce neutrons. Neutrons produced from the DT reaction are emitted uniformly in all directions from the target, i.e., isotropically, while neutrons from the DD reaction are slightly peaked in the forward direction. In both cases, the associated He nuclei (alpha particles) are emitted in the opposite direction of the neutron.

When measuring uranium, the spontaneous fission rate produces about 13 neutrons per second per kilogram of U238 and less for U235. At this count rate, it might take on the order of day of counting to see the correlated fission signal from uranium. To speed this process, systems may use an external neutron source to induce fission in the U235. Using an isotopic neutron source means the user must carry radioactive material, which is undesirable. An alternative approach is to use an electrically generated neutron source, commonly available in the form of DD or DT electric neutron sources.

In a further alternative embodiment, a 60 keV neutron source may be used to operate below the U238 fission threshold. In general, the fact that the energy is above the fission threshold is not an issue because inducing fission is the objective. One simply needs to keep track of which sources are counted in the Poisson or fission category. With regard to the alternative embodiment, the 60 KeV neutron source may be configured as described in U.S. patent application Ser. No. 12/976,216, which is assigned to the assignee of the present application, and which is incorporated herein by reference in its entirety.

The electric neutron sources are intended to be either pulsed or steady state in neutron production. Electric neutron sources are regularly used to induce fission, where the user irradiates a sample, and looks for delayed neutrons as a signal that fissile material is present. The delayed neutrons created amount to about 2% of the fissions induced by the electric neutron source. This method requires injecting such a large number of neutrons that the operation is hazardous to humans. Typical neutron interrogators supply $10^8$ to $10^{10}$ neutrons per second and supply neutrons for about ten minutes. The neutron generator is then turned off and the neutron counter counts any delayed neutrons to indicate fissile material is present.

An alternative to observing the delayed neutron fraction is to look for neutrons produced while the interrogation beam is on. This improves system efficiency significantly (such as up to about 5000%) since the duty factor is about 100%, in this type of system. Directly observing the promptly induced fission neutrons requires that the neutron detector be able to distinguish the electric source neutrons and the induced fission neutrons, which until now has been impractical with the very portable DD or DT electric neutron sources. An example of an impractical energy selection method is a time-of-flight energy spectrometer, which obtains very high energy selectivity by dispersing the two sources of neutrons over a 100 meter long path. This energy selectivity approach is still not ideal since both the electric neutron sources and induced fission make overlapping neutron energies, making a clean separation impossible. Energy resolving neutron spectrometers, in the form of hand-held detectors, resolve neutron energies so inefficiently that they are not used with the common DD and DT electric neutron generators.

To overcome this disadvantage, embodiments are directed to a superior method to detect fissile or fertile nuclear material using a novel neutron source that facilitates distinguishing of the two sources of neutrons using a multiplicity counter. This method enables the use of the common DD or DT neutron generators. A special feature of the interrogator is the random or Poisson time correlation of the neutrons produced by the DD or DT electric source, coupled with a multiplicity counter to observe any correlation. Any correlation would mean fission was induced and therefore fissile or fertile material is present.

In general, DD and DT electric neutron sources actually produce some amount of correlated neutrons because their electric drive circuits are actually time-varying, imprinting the high voltage ripple on the neutron output. Ripple is small unwanted residual periodic variation of the DC output of a power supply which has been derived from an AC source, such as due to incomplete suppression of the alternative waveform in the supply. This problem has forced all prior neutron interrogation methods to induce fission, then turn off the neutron source, after which the user measures the delayed neutron activity, which only comes as a result of inducing fission. The pulsed neutron sources produce correlated neutrons, by definition, since they are pulsed with the AC ripple adding correlation. Therefore, the "steady state" versions of the DD and DT sources have been, in reality, not steady state, and therefore not Poisson.

In general, Poisson DD or DT generators are always made with an AC rectifying high voltage DC supply. As stated above, the problem with all DD and DT generators is the presence of ripple on the DC supply. This ripple can significantly correlate the neutron production, defeating the expectation there will be no detected correlation in the absence of fissile material. It is the significant amount of correlation in DD and DT neutron generators that requires all commercial waste assay counters to count only the delayed fraction of induced neutrons, which is an inefficient process, as described above. One approach to make a Poisson DD or DT neutron generator is to simply filter the AC component from the high voltage DC. However, this filtering technique does not work in a portable instrument because the components that would operate at the required 120,000 volts would be larger than someone could carry.

Figure 8:
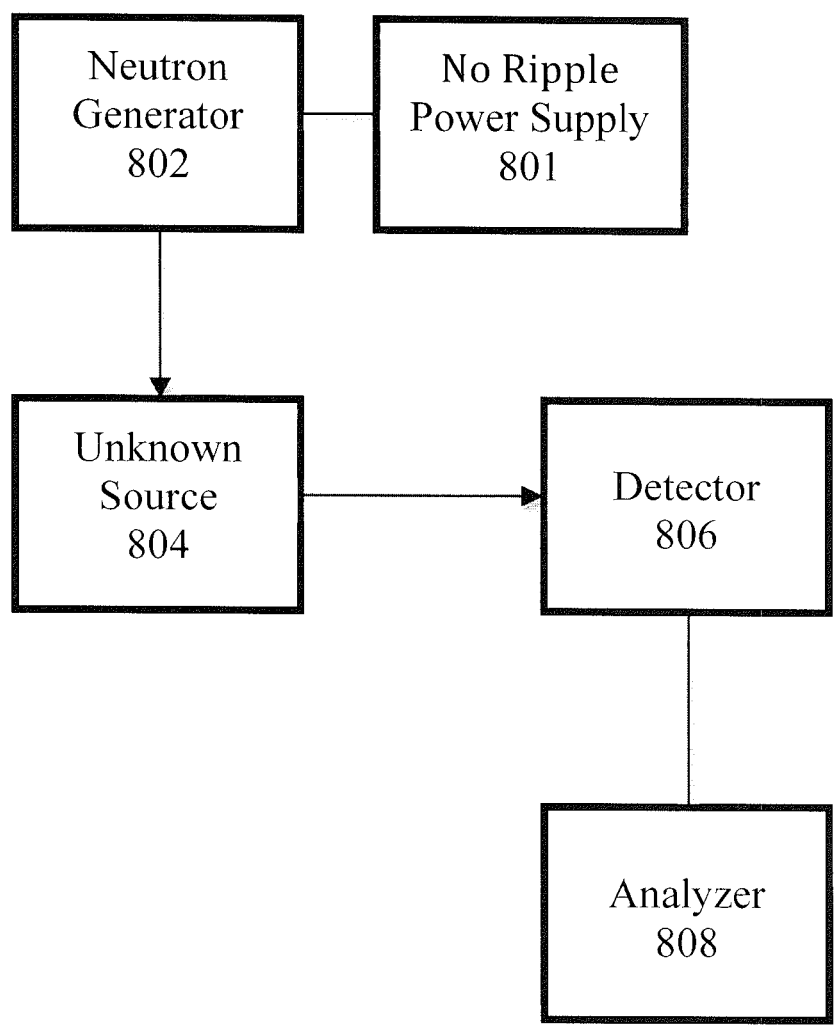
FIG. 8 illustrates a neutron detection system including a Poisson neutron electric source, under an embodiment.

To address this disadvantage, embodiments are directed to a steady state neutron generator coupled with a multiplicity counter that incorporates a circuit that strongly filters the AC from the high voltage DC signal, along with an algorithm that indicates the presence of neutron correlation and provides a corresponding alarm system. This system is embodied in a Poisson electric neutron source that observes any induced neutron correlation as an indication of fission, thereby detecting fissile or fertile material. In an embodiment, such as system may be packaged in a device that weighs less than 100 pounds. FIG. 8 illustrates a neutron detection system including a Poisson neutron electric source, under an embodiment. As shown in system 800 of FIG. 8, a neutron generator 802 of either a DD or DT electric neutron source type is used to irradiate the unknown source 804 that is to be characterized. The neutron generator is meant to induce fission in the unknown source. The detector 806 detects neutrons produced by the neutron source in a direct rather than delayed manner. The detector distinguishes between the electric source neutrons from generator 802 and the induced neutrons from source 804. The detector 806 is coupled to analyzer 808, which includes a multiplicity counter function to observe any correlation in the detected neutrons. In an embodiment, the multiplicity counts are processed in accordance with methods described with respect to FIGS. 3A to 3C earlier. To eliminate the effect of electrical ripple or other distortion effects caused by power supply circuitry, the neutron generator is powered by a no-ripple power supply 801.

In an embodiment, the detector 806 of FIG. 8 may include two or more different detector circuits to detect and distinguish neutrons of different sources. For example, background neutrons from alpha-n reactions are Poisson and have a unique count distribution shape, cosmic induced neutrons are created in the nanosecond scale and have their own unique count distribution shape, and fission neutrons are created over a time-scale controlled by the relatively slow fission neutron speed, which guarantees fission signatures that form in greater than tens of nanosecond time scales up to milliseconds. To take advantage of these distinctions, the detector 806 may comprise at least two types of detectors. In an embodiment, detector 806 includes a scintillator with an energy selector that guarantees only fast and direct neutrons are counted and a moderated neutron capture detector (He3, Boron, Lithium) for the slower times scales. Either detector may be embodied as a separate detector within system 800 or part of an integrated or combined detector circuit 806. In certain cases, the scintillator may also be used for the slower time scales. Other types of detectors that distinguish neutrons generated on a short time scale (e.g., nanosecond) versus longer time scales (e.g., milliseconds) can also be used.

As shown in FIG. 8 embodiments include a Poisson neutron source that features a characteristic for the DC supply of having a ripple less than one part per million. At present for applications requiring 120,000 volts, there are no such DC supplies. The process for filtering the DC cannot be lumped RLC (resistor-inductor-capacitor) circuits since their voltage stand-off and power dissipation needs would require a dielectric chamber of several feet in dimension, exceeding the volume of the normal 120,000 volt supply. The Poisson neutron source under an embodiment, has two power supplies that have their outputs summed, with the sinusoidal ripple added 180 degrees out of phase. A Cockroft-Walton voltage multiplier is also used. The frequency of the Cockroft-Walton voltage multiplier is increased to enhance the effectiveness of series RL circuit components. Such a circuit significantly reduces ripple on the output DC signal.

Figure 9:
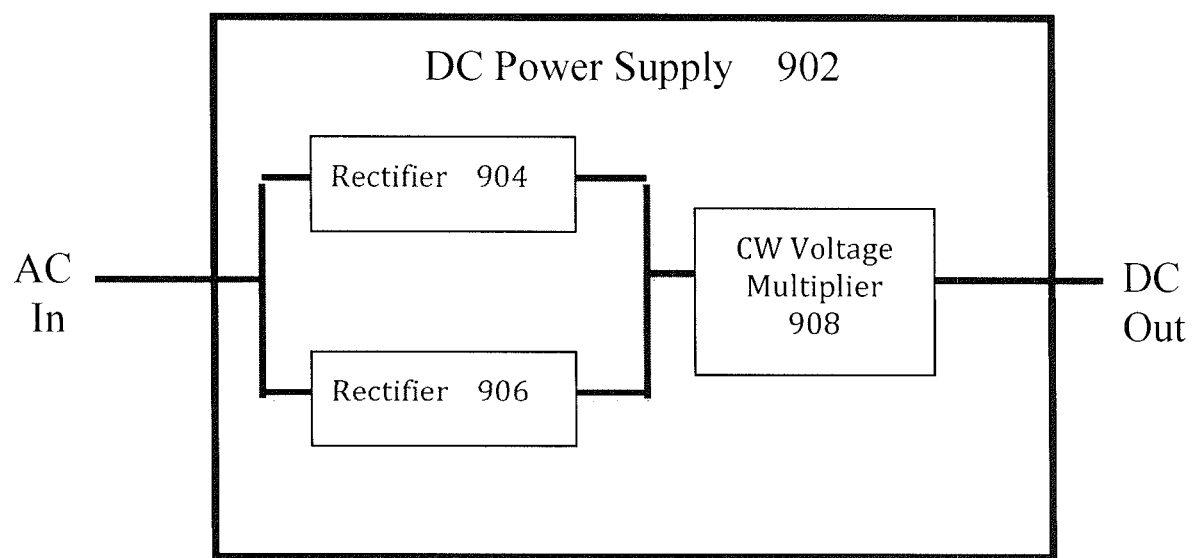
FIG. 9 is a block diagram of a no-ripple DC power supply for use in a Poisson neutron electric source, under an embodiment.

FIG. 9 is a block diagram of a no-ripple DC power supply for use in a Poisson neutron electric source, under an embodiment. As shown in diagram 900, DC power supply 902 receives AC electricity in and passes this AC input to two separate rectifier stages 904 and 906. The rectifier circuits convert the AC into DC electricity through known rectification methods. In most practical circuits, at least some amount of ripple will be present on the DC signals that are output from the rectifiers 904 and 906. The output stages of the rectifiers are coupled together such that the ripple components are added together 180 degrees out of phase. This effectively cancels the ripple present on the DC outputs of both the rectifiers when the signals are added together. The summed DC signal is then input to a Cockroft-Walton voltage multiplier 908 to bring the level of the DC output signal up to a desired level.

In general, a Cockroft-Walton voltage multiplier (or generator) is a circuit that generates a high DC voltage from a low voltage AC or pulsing DC input. It comprises a voltage multiplier ladder network of capacitors and diodes to generate high voltages. In an alternative embodiment, other similar voltage multiplier circuits may be used.

The neutron detection system under an embodiment includes a Poisson neutron source, coupled with the utility of an instrument that can observe that such a source is or is not Poisson, coupled with an alarm that is sensitive to the distinction between Poisson and correlated neutrons. Such a system is implemented to operate in an in-beam mode (prompt fission neutrons) that is much more efficient than previous delay-based systems that require turning off the neutron interrogator prior to neutron detection. A side benefit of this systematic approach is to use the large increase in total efficiency to reduce the interrogation source strength by about a factor of 100, making portable field use much safer.

The use of a Poisson neutron source for use in in-beam interrogation systems that imposes virtually no ripple to distort the correlation of generated neutrons in a neutron detection system reduces or eliminates the problematic effect of electrical ripple on the DC supply that can cause correlation of neutron product.

Time Scales and Scintillators

In an embodiment, the detector system includes a multiplicity counter function that uses the inherent time scales that define the correlation rate that neutron counts arrive at the detector. Thus, as described above, different time-scale detectors may be used in the detection and analysis system 800 of FIG. 8. Given the timing nature inherent in the definition of gate width, one may simply categorize and distinguish the time scales over which the correlated signals arrive. For example, the time scale for cosmic spallation induced neutrons is on the order of a few nanoseconds as compared to fission chains, which must evolve over at least tens of nanoseconds. With a gate setting of three nanoseconds any correlation must be from cosmic background and may be used as the definition of the count rate for this background and may therefore be used as a measure of how much count rate must be coming from non-background sources. Similarly, the alpha-induced Poisson background from either the soil or an intentionally added interrogation source may be removed from the total signature by the methods described in references such as U.S. Pat. Nos. 8,194,813 and 8,194,814, which both are assigned to the assignee of the present application and are hereby incorporated by reference in their entirety. This leaves the user with a numerical excess in count rate and a multiplicity distribution that defines the slowly evolving fission signature.

As taught in the above-referenced U.S. Pat. Nos. 8,194,813 and 8,194,814, correlation in count distributions may be converted to a linear space within which count rates may be subtracted, or sums of big-Lambda distributions may be fit in an error minimization scheme. Beyond this novelty in how to add and subtract, is the next critical breakthrough that allows one to directly benefit from the time scales within which any correlation arrives. As an example in the distinction, a scintillator responding to neutrons reports a count to the electronics counter in about two nanoseconds. Instead of only looking at the count distributions that form in the microsecond to millisecond time scales, there is an opportunity to look at the nanosecond time scales. The benefit is that cosmic spallation produced neutron clusters are formed in time scales of nanoseconds (i.e., 3 ns). With a neutron detector like the scintillator, this fraction of neutron counts forming correlation may be directly and distinctively quantified, using the herein described linear space methods. For the purposes of detecting fissionable material, simply quantifying the Poisson portion of the detected signal, the cosmic induced portion and removing them from the total leaves the net total as the basis in the method to define detection of fissionable material. The novel combination of methods is most generally based on recognition of the time scale over which the correlation arrives and recognizing the shape of this correlation in the form of the count distribution.

As stated previously, neutrons from different sources have different signatures with respect to the time-scale and distribution of emission. Specifically, background neutrons from alpha-n reactions exhibit a Poisson distribution, cosmic induced neutrons are created in the nanosecond scale, and fission neutrons are created over a time scale on the order of greater than tens of nanoseconds to milliseconds. One or more appropriate detector circuits are provided to detect the emitted neutrons relative to these different time scales and/or emission patterns. The system provides combinations or subset selection of a known signature neutron source, selection of the necessary correlation time scales, distribution shapes, and detector time-response specification to enable mathematically precise access to the signatures required in a particular detection system.

In one embodiment, the neutron detector system described herein can be embodied within a portable device that can be deployed in the field and used by personnel to detect the presence of potentially dangerous sources of radioactive material from virtually any type of object or item. The packaging around any such source can be shielded or unshielded. Such a detector system can also be used in any type of Nuclear Instrumentation Module (NIM) for use in experimental particle or nuclear physics.

Embodiments of the present invention are suitable to provide a simple, quick approach that minimally trained operators can use to improve the control of fissioning material. The operators, for example may include border or traffic police, baggage handlers or freight companies, or for international treaty agreements that endeavor to identify, segregate, or manage inventories of nuclear material.

Aspects of the circuitry and methodology may be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: microcontrollers with memory (such as EEPROM), embedded microprocessors, firmware, software, etc. Furthermore, aspects of the memory test process may be embodied in microprocessors having software-based circuit emulation, discrete logic (sequential and combinatorial), custom devices, fuzzy (neural) logic, quantum devices, and hybrids of any of the above device types. As is understood in the art of electronic circuit manufacture, a number of different underlying device technologies may be provided in a variety of component types.

It should also be noted that the various functions disclosed herein may be described using any number of combinations of hardware, firmware, and/or as data and/or instructions embodied in various machine-readable or computer readable media, in terms of their behavioral, register transfer, logic component, and/or other characteristics.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list. While embodiments may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A system for characterizing a radiation source as fissile material or non-fissile material, comprising:
   a DC power supply comprising an AC filter circuit;
   a neutron generator coupled to the DC power supply and configured to irradiate the radiation source by inducing radiation in the radiation source;
   a detector configured to receive and count neutrons emitted from the radiation source both naturally and from irradiation by the neutron generator; and
   an analyzer component coupled to the detector and configured to measure a number of neutrons simultaneously emitted from the radiation source during a number of measurement time periods to derive a multiplet count distribution, compute the mean count rate of the multiplet count distribution, compute the number of pairs of the multiplet count distribution, use the mean count rate to produce a Poisson distribution for the mean count rate, compute the expected number of pairs for the Poisson distribution, subtract the expected number of pairs for the Poisson distribution from the number of pairs in the measurement, and characterize the radiation source as fissile material if the number of pairs in the measurement exceeds the number of pairs for the Poisson distribution.

2. The system of claim 1 wherein the AC filter circuit comprises:
   an AC receiving circuit;
   a pair of rectifiers converting an input AC signal to respective DC output signals;
   a summer circuit receiving the respective DC output signals and configured to add the respective DC output signals together by adding electrical ripple present on a DC output signal from one rectifier of the pair of rectifiers 180 degrees out-of-phase to the electrical ripple present on a DC output signal from the second rectifier of the pair of rectifiers; and a Cockroft-Walton voltage multiplier circuit coupled to the summer circuit and configured to increase the output of the summed DC output signals to a desired DC voltage level.

3. The system of claim 2 wherein the analyzer component is further configured to:

produce a hypothetical histogram for the Poisson distribution;

produce a count histogram for the count measurement representing a number of times different group sizes occur from the number of measurement time periods; and overlay the histogram and Poisson count distribution to make a mean count of the hypothetical histogram the same as for the count histogram and to provide a visual indication of the difference in correlation of emitted neutrons from the radiation source, to characterize the neutron source as fissile material or non-fissile material.

4. The system of claim 3 further comprising a component to determine the value of a coefficient, Cn, which represents a number of times that a group of neutrons is observed after repeating a ½ millisecond measurement time period a defined number of times, and wherein the mean count is calculated by the formula:

$$\overline{C} = \frac{\sum_{n=0}^{\infty} nCn}{\sum_{n=0}^{\infty} Cn}.$$

5. The system of claim 4 wherein the shape of the histogram representation of the count measurement is given by the formula:

$$Cn\text{-poisson} = \frac{\overline{C}^n}{n!}e^{-\overline{C}}.$$

6. The system of claim 1 wherein the neutron generator comprises a pulsed electric source of neutrons irradiating the radiation source using an interrogation beam of neutrons.

7. The system of claim 1 wherein the detector comprises:

a first detector calibrated to a fast time scale on the order of nanoseconds to generate a first set of detected neutrons; and a second detector calibrated to a slow time scale on the order of milliseconds to generate a second set of detected neutrons.

8. The system of claim 7 wherein the analyzer is configured to analyze the first and second sets of detected neutrons to determine the number of times that a group of n simultaneously emitted neutrons is observed from the radiation source after a defined measurement period is repeated a defined number of times to derive a neutron count measurement based on at least one of the fast time scale and slow time scale to determine whether the material is fissile versus non-fissile.

9. The system of claim 8 wherein the defined measurement time period is ½ millisecond, and wherein a fissile source creates real correlations between the neutrons emitted from the radiation source, and a non-fissile source creates no correlation or only accidental correlations between the neutrons emitted from the radiation source.

10. The system of claim 7 wherein the first detector comprises a scintillator and energy selector system that is configured to detect fast and direct neutrons emitted from the material.

11. The system of claim 10 wherein the second detector comprises at least one of a moderated neutron capture detector or a scintillator-based detector, both configured to detect neutrons emitted from the material in correspondence with the slow time scale.

* * * * *